United States Patent
Björklund et al.

(10) Patent No.: US 6,350,257 B1
(45) Date of Patent: Feb. 26, 2002

(54) ABSORBENT ARTICLE WITH HIGH STIFFNESS

(75) Inventors: Camilla Björklund, Mölnlycke; Urban Widlund, Pixbo; Ann Samuelsson, Lindome; Solgun Drevik, Mölnlycke; Anders Gustafsson, Billdal, all of (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/297,365
(22) PCT Filed: Nov. 11, 1997
(86) PCT No.: PCT/SE97/01881
§ 371 Date: Aug. 2, 1999
§ 102(e) Date: Aug. 2, 1999
(87) PCT Pub. No.: WO98/22057
PCT Pub. Date: May 28, 1998

(30) Foreign Application Priority Data

Nov. 15, 1996 (SE) .............................. 9604223

(51) Int. Cl.⁷ ............................................. A61F 13/15
(52) U.S. Cl. ............................ 604/385.01; 604/385.17
(58) Field of Search ................... 604/385.01, 385.17

(56) References Cited

U.S. PATENT DOCUMENTS

| | | |
|---|---|---|
| 810,119 A | 1/1906 | Green |
| 810,120 A | 1/1906 | Green |
| 810,131 A | 1/1906 | Green |
| 1,946,626 A | 2/1934 | Jurgensen |
| 2,551,663 A | 5/1951 | Fox |
| 3,407,814 A | 10/1968 | George et al. |
| 3,468,311 A | 9/1969 | Gallagher |
| 3,570,493 A | 3/1971 | Olsson |
| 3,888,255 A | 6/1975 | Shah et al. |
| 4,041,950 A | 8/1977 | Jones, Jr. |

(List continued on next page.)

FOREIGN PATENT DOCUMENTS

| | | |
|---|---|---|
| EP | 0 067 377 A2 | 12/1982 |
| EP | 0 155 515 A1 | 9/1985 |
| EP | 0 235 763 A1 | 9/1987 |
| EP | 0 335 252 A2 | 10/1989 |
| EP | 0 335 253 B1 | 10/1989 |

(List continued on next page.)

OTHER PUBLICATIONS

U.S. application No. 09/297,366, filed Jul. 7, 1999; Inventors: Anette Johansson et al. (WO 98/22060).
U.S. application No. 09/297,584, filed Aug. 12, 1999; Inventors: Camilla Björklund et al. (WO 98/22058).

(List continued on next page.)

*Primary Examiner*—Dennis Ruhl
(74) *Attorney, Agent, or Firm*—Burns, Doane, Swecker & Mathis, L.L.P.

(57) ABSTRACT

The invention relates to an absorbent article such as a sanitary napkin, an incontinence guard, or a panty-liner, which article has a generally elongated shape with a longitudinal direction and a transverse direction and exhibits two side edges (9, 10), two end portions (6, 7), and a crotch portion (8) located between the end portions (6, 7), which article further exhibits a liquid-pervious cover layer (2), intended to be facing the user during use, and a liquid-impervious cover layer (3), intended to be facing away from the user during use. The article comprises at least within the crotch portion (8) a stiffening element (15) of a material with a very high intrinsic stiffness, whereby the article in the crotch portion (8) has an extension in the transverse direction which during use of the article is between 40 mm and 15 mm and preferably is between 20 mm and 35 mm.

16 Claims, 3 Drawing Sheets

U.S. PATENT DOCUMENTS

| | | |
|---|---|---|
| 4,047,531 A | 9/1977 | Karami |
| 4,195,634 A | 4/1980 | DiSalvo et al. |
| 4,217,901 A | 8/1980 | Bradstreet et al. |
| 4,351,340 A | 9/1982 | McLeod |
| 4,386,932 A | 6/1983 | Pitts |
| 4,536,181 A | 8/1985 | Cook |
| 4,643,726 A | 2/1987 | Gegelys |
| 4,673,403 A | 6/1987 | Lassen et al. |
| 4,804,380 A | 2/1989 | Lassen et al. |
| 4,828,555 A | 5/1989 | Hermansson |
| 4,846,824 A | 7/1989 | Lassen et al. |
| 4,865,597 A | 9/1989 | Mason, Jr. et al. |
| 4,897,084 A | 1/1990 | Ternström et al. |
| 4,911,701 A | 3/1990 | Mavinkurve |
| 5,032,121 A | 7/1991 | Mokry |
| 5,074,855 A | 12/1991 | Rosenbluth et al. |
| 5,074,856 A | 12/1991 | Coe et al. |
| 5,080,658 A | 1/1992 | Igaue et al. |
| 5,098,422 A | 3/1992 | Davis et al. |
| 5,114,419 A | 5/1992 | Daniel et al. |
| 5,129,893 A | 7/1992 | Thorén |
| 5,171,302 A * | 12/1992 | Buell .................... 604/385.01 |
| 5,181,563 A | 1/1993 | Amaral |
| 5,197,959 A | 3/1993 | Buell |
| 5,295,987 A | 3/1994 | Widlund et al. |
| 5,354,400 A | 10/1994 | Lavash et al. |
| 5,374,260 A | 12/1994 | Lemay et al. |
| 5,383,868 A | 1/1995 | Hyun |
| 5,454,802 A | 10/1995 | Lindquist et al. |
| 5,460,623 A | 10/1995 | Emenaker et al. |
| 5,545,156 A | 8/1996 | DiPalma et al. |
| 5,558,656 A | 9/1996 | Bergman |
| 5,569,231 A | 10/1996 | Emenaker et al. |
| 5,591,150 A | 1/1997 | Olsen et al. |
| H1634 H | 2/1997 | Oetjen et al. |
| 5,624,421 A | 4/1997 | Dabi et al. |
| 5,688,259 A | 11/1997 | Osborn, III et al. |
| 5,695,324 A | 12/1997 | Weirich |
| 5,704,931 A | 1/1998 | Holtman et al. |
| 5,722,967 A | 3/1998 | Coles |
| 5,741,241 A | 4/1998 | Guidotti et al. |
| 5,827,258 A | 10/1998 | McFall et al. |
| 5,849,003 A | 12/1998 | Olsen et al. |
| 5,873,869 A | 2/1999 | Hammons et al. |
| 5,919,178 A | 7/1999 | Widlund |
| 5,957,909 A | 9/1999 | Hammons et al. |
| 5,961,508 A | 10/1999 | Mayer et al. |
| 6,020,536 A | 2/2000 | Osterdahl et al. |
| 6,033,391 A | 3/2000 | Osborne, III et al. |
| 6,042,575 A | 3/2000 | Osborn, III et al. |
| 6,080,909 A | 6/2000 | Osterdahl et al. |

FOREIGN PATENT DOCUMENTS

| | | |
|---|---|---|
| EP | 0 335 253 A1 | 10/1989 |
| EP | 0 336 578 A1 | 10/1989 |
| EP | 0 155 515 B1 | 12/1989 |
| EP | 0 339 041 B1 | 11/1991 |
| EP | 0 419 434 B2 | 5/1993 |
| EP | 0 606 082 A1 | 7/1994 |
| GB | 2 119 656 | 11/1983 |
| GB | 2 119 657 | 11/1983 |
| WO | 92/19197 | 11/1992 |
| WO | 93/15702 | 8/1993 |
| WO | WO 93/21879 | 11/1993 |
| WO | 95/31165 | 11/1995 |
| WO | 96/20679 | 7/1996 |
| WO | 96/26699 | 9/1996 |
| WO | WO 97/09015 | 3/1997 |
| WO | 98/22058 | 5/1998 |

OTHER PUBLICATIONS

U.S. application No. 09/297,583, filed Aug. 3, 1999; Inventors: Anders Gustafsson et al. (WO 98/22059).

U.S. application No. 09/297,637, filed Aug. 4, 1999; Inventors: Camilla Björklund et al. (WO 98/22061).

U.S. application No. 09/297,746, filed Sep. 1, 1999; Inventors: Ann Samuelsson et al. (WO 98/22062).

* cited by examiner

ABSORBENT ARTICLE WITH HIGH STIFFNESS

TECHNICAL FIELD

The invention relates to an absorbent article such as a sanitary napkin, an incontinence guard, or a panty-liner, which article has a generally elongated shape with a longitudinal direction and a transverse direction and also exhibits two side edges, two end edges, two end portions, and also a crotch portion located between the end portions, which article further exhibits a liquid-pervious cover layer, intended to be facing the user during use, and also a liquid-impervious cover layer, intended to be facing away from the user during use.

BACKGROUND OF THE INVENTION

When using an absorbent article such as a sanitary napkin, an incontinence guard or the like, with a relatively small size and intended to principally be able to be accommodated in the crotch region of a user, it is a significant problem that the article during use is deformed by the forces which arise for example when the user moves about. Since the article is subjected to compression between the legs of the user, creases and ruptures arise in an uncontrolled manner in the absorbent body of the article as well as in its liquid-pervious cover layer. This is of course a disadvantage, since wrinkles act as liquid-conducting channels, in which liquid may flow out over the edges of the article. Furthermore, ruptures in an absorbent body lead to deterioration of the liquid-distributing ability in the absorbent body, so that the liquid stays in the acquisition region of the article, i.e. in the region which first is wetted by the liquid. Thereby, the risk of the acquisition region being supersaturated by liquid is imminent, entailing an increased risk of leakage.

There is also a significant risk that the side edges of the article during use are folded in over the liquid-pervious surface, so that the portion of the article which is directly accessible for reception and absorption of liquid is considerably reduced. Also deformation of this type increases the risk of leakage.

Another significant problem associated with the fact that an absorbent article is deformed during use, is that the article becomes wrinkled and lumpy and feels uncomfortable to wear. At worst, sharp and chafing creases are formed which irritate the skin of the user during use.

In U.S. Pat. No. 4,217,901 a sanitary napkin comprising a compressed layer of fluff pulp is disclosed, which layer serves to increase the resistance towards deformation of the sanitary napkin. Unfortunately, a fluff pulp layer loses its stiffness when wetted, whereby the previously known sanitary napkin only exhibits an elevated stiffness in an initial stage of use. Furthermore, a loosening of the compressed fluff pulp layer takes place during use, depending on the fact that the fibres of the layer are torn apart when the sanitary napkin is subjected to tension and pressure forces during use. A further disadvantage with the previously known compressed fluff pulp layer is that it substantially lacks resilience, which implies that a layer that has been cracked or otherwise deformed does not have the ability to regain its original shape.

SUMMARY OF THE INVENTION

By means of the present invention an article of the type discussed in the introduction has been achieved, in which the disadvantages and problems which are associated with such previously known articles have been essentially eliminated. An article designed in accordance with the invention is thereby mainly characterized in that the article, at least within the crotch portion, comprises a stiffening element of a material with a very high intrinsic stiffness, whereby the article within at least a part of the crotch portion has a dimension in the transverse direction which, when the article is used, is between 15 mm and 40 mm and preferably is between 20 mm and 35 mm.

Since the article comprises a component with a very high stiffness, the risk of uncontrolled deformation by means of transverse compression has been completely eliminated. The article according to the invention primarily has the ability to resist compression when it is subjected to the forces which arise between the legs of the user during use.

According to a preferred embodiment of the invention, the stiffening element can only be compressed to approx. 80% of its original width during compression of the crotch region in the transverse direction of the article with forces of the magnitude which are present during use.

Measurements have shown that all humans have a critical area in the groin portion between two muscle groups which extend from the inside of the pelvis bottom down along each thigh. The distance between the two muscle groups has thereby been found to be surprisingly similar for all humans, independently of body shape and weight. Thus, the distance between the thighs of a user is of course affected by fatness, while the distance between the muscle groups in the crotch of the user is the same, independently of whether the user is thin, of normal weight or overweight. It was shown that the factor which decides if a user experiences discomfort in the form of pressure or chafing against the insides of the thighs is whether the absorbent article during use has a width which in the critical area considerably exceeds the distance between the muscle groups in the groin area. This distance has been found to be between approx. 30 mm and 35 mm, Furthermore, it has been provided that an article with a width which during use exceeds 40 mm in the critical area is perceived as uncomfortable by the majority of users. On the contrary, it is seldom perceived to be unpleasant that an absorbent article presses against or displaces fatty tissue which may occur in the crotch area.

In the case of conventional deformable absorbent articles, the limited space in the crotch region of the user entails that the articles are compressed in an uncontrolled way between the legs of the user and are creased in order to be accommodated in the groin area. Where an absorbent article according to the invention is concerned, having a very stiff shape-retaining element in the crotch portion, compressing may only take place to a limited extent, whereby the degree of possible compression is controlled by the design of the stiff crotch portion. It is therefore essential that the width of the absorbent article in the crotch portion during use does not exceed the critical value which can be tolerated by the user.

Thereby, however, it is not necessary that the crotch portion along its entire length has a width which during use is below 40 mm. Since the critical area in the crotch region of the user is approx. 5 mm to 15 mm long, it is sufficient if the part of the crotch portion which is intended to be arranged within this area during use fulfils the requirement of a maximum width. Accordingly, it is sufficient for the invention if, in the longitudinal direction of the article, there is a 5–15 mm long area in the crotch potion within which the width during use of the article is not greater than approx. 40 mm and preferably is not greater than approx. 35 mm.

A suitable stiffening element is profiled in the transverse direction of the article and exhibits at least one longitudinally extending ridge, or furrow. Thereby, a longitudinal ridge with rounded surface may be arranged along each side edge of the article at least at the crotch portion. An absorbent article according to the invention is advantageously provided with a centrally arranged longitudinal hump. Thereby, a longitudinal furrow may be arranged at each side of the central hump, between this and the side edges of the article. Advantageously, longitudinal ridges are combined with lowered portions, or furrows.

Furthermore, transverse compression of the article in the vicinity of the transition area between the crotch portion and the front portion affects the stiffness of the article during use. Such compression increases the beam effect rendered by the stiffening element and counteracts bending of the front portion in relation to the crotch portion.

Thus, the stiffness of an absorbent article depends to a high degree on the shape of the article, particularly the shape of the stiffening element. Consequently, a stiffening element with beams in the form of ridges or furrows has a higher stiffness, perpendicularly to the extension of the ridges or the furrows, than a completely flat material. The beams may be obtained by forming the material itself, or by reinforcing it with strips or ribs of a separate material. Furthermore, the stiffness and the resistance to bending and twisting may be increased by imparting a bowl-shape to the material, or by means of increased material thickness.

As examples of plastic materials which have been found to have sufficient bending stiffness and torsional rigidity in order to achieve the ability to resist uncontrolled deformation which is necessary for the invention, polyethylene or polypropylene with a layer thickness of at least 0,4 mm may be mentioned. Furthermore, it is possible to increase the stiffness of a plastic layer by mixing the plastic with talc, chalk, or other stiffness-increasing fillers. The material stiffness of a plastic film which is suitable for use as a stiffening element in an article according to the invention should thereby exceed 100 N, measured in accordance with ASTM D 4032-82 "Circular Bend Procedure", which method is described in detail in EP 0 336 578. In this context, material stiffness refers to the stiffness of a flat material layer.

Furthermore, it is possible to use plates, rods, skeleton-like constructions or the like of metal, wood or other stiff materials which do not substantially change their stiffness properties when wetted, and are not broken by the forces which arise during use of an absorbent article. Accordingly, it is possible to use, for instance, cardboard which has been treated in order to resist wetting for example by means of coating with plastic or the like in order to prevent that the material softens when wetted and in order to increase the toughness of the material and to reduce the risk of breaking. It is not completely essential for the invention that the stiffening element is constituted by a continuous material layer, but stiffening elements composed off stiff beams, tubes, pegs, or the like may also be used. A stiffening element which thereby has been found to perform particularly well is a skeleton-like structure of bent metal rods. On condition that such a structure conforms well to the anatomy of the user and, particularly, does not exceed the critical width in the crotch region of an absorbent article, such a metal skeleton maybe allowed to be completely incompressible by such forces which occur during normal use.

When very rigid stiffening elements are used it may be desirable to arrange soft, easily deformable edge portions on both sides along the side edges of the article. Such an arrangement allows for a certain amount of compression of the article in the transverse direction and, at the same time, provides the article with soft, comfortable edges.

An anatomically designed article according to the invention is kept securely and comfortably in position against the body of the user during use, without the need for special attachment means. This implies that the article is completely unattached to the panties of the user, whereby the risk that the article during use moves with the panties and thereby ends up in an incorrect position in relation to the body of the user is almost completely eliminated.

BRIEF DESCRIPTION OF THE DRAWINGS

The invention will in the following be described in greater detail with reference to the embodiments which are shown in the attached drawings, Thereby.

DETAILED DESCRIPTION OF PREFERRED EMBODIMENTS

Figure 1:
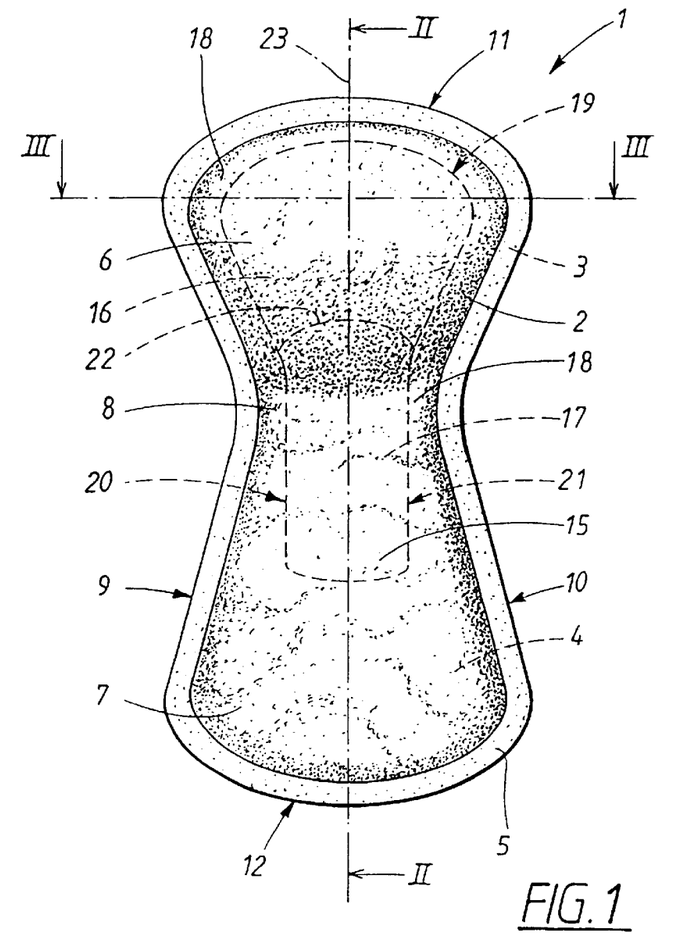
FIG. 1 shows a sanitary napkin according to the invention.
Figure 2:
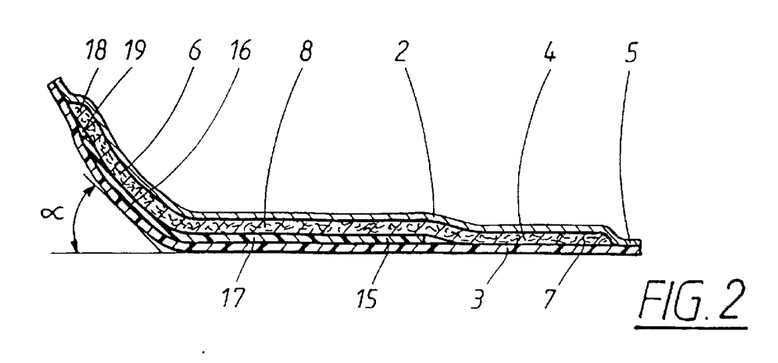
FIG. 2 shows a section along the line II—II through the sanitary napkin in FIG. 1.
Figure 3:
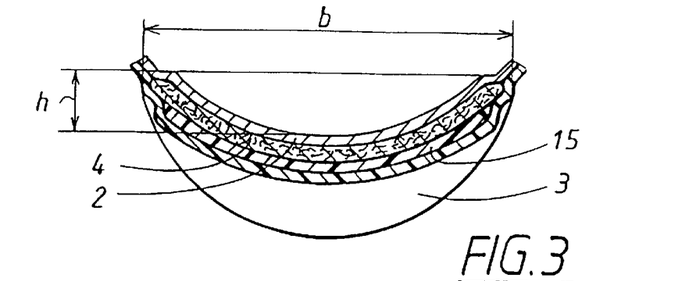
FIG. 3 shows a section along the line III—III through the sanitary napkin in FIG. 1.

The sanitary napkin 1, shown in FIGS. 1, 2 and 3, comprises a liquid-pervious cover layer 2, arranged on the side of the sanitary napkin 1 which during use is intended to be facing the user, a liquid-impervious cover layer 3, arranged on the side of the sanitary napkin 1 which during use is intended to be facing away from the user, and an absorbent body 4, enclosed between the two cover layers 2, 3.

The material of the liquid-pervious cover layer 2 may be, for example, a perforated plastic film, a plastic scrim or a textile material, a nonwoven material or a laminate of, for example, a perforated plastic layer and a nonwoven layer. The plastic is typically a thermoplastic, such as polyethylene or polypropylene. The expression nonwoven material refers to a non-woven fibre fabric. Suitable nonwoven materials may consist of natural fibres such as cellulose or cotton, or synthetic fibres such as polyethylene, polypropylene, polyester, polyurethane, nylon or regenerated cellulose, Naturally, it is also possible to use nonwoven materials made from fibre blends.

The liquid-pervious cover layer 2 shall receive and conduct the liquid into the absorbent body 4. Furthermore, the cover layer 2 should be soft and pleasant against the body of the user, and also be able to prevent so-called rewetting, i.e. that absorbed body exudate forces its way back towards the sin of the user. For reasons of comfort, and in order to avoid skin irritation, it is important that the surface on the part of the sanitary napkin which is in contact with the skin of the user is maintained as dry as possible during use. Furthermore, a dry surface on the sanitary napkin is perceived by the user as being cooler and more pleasant during use, and is both from a purely visual point of view and when handling the sanitary napkin when this is to be replaced, more pleasant than a soiled, wet surface.

It is not necessary for all embodiments of the invention that the liquid-pervious cover layer 2 in fact is constituted by a separate material layer. The liquid-pervious cover layer may, for instance, constitute an integral part of an absorbent body. Consequently, it is conceivable to exclude the liquid-pervious cover layer when the absorbent body comprises an absorbent foam layer. Furthermore, an absorbent nonwoven material may be utilized, which may be an integral component of an absorbent body and at the same time constitute a liquid-pervious cover layer.

The liquid-impervious cover layer 3 consists of a liquid-impermeable material. Thin, liquid-impervious plastic films are suitable for the purpose. However, it is also possible to use materials which are liquid-pervious to start with, but which have been furnished with a coating of plastic, resin, or other liquid-impervious material. Thereby, leakage of liquid from the bottom side of the absorbent article is prevented. The liquid-impervious cover layer 3 may, accordingly, consist of any material which is skin-friendly and fulfils the criteria of liquid-impermeability. Examples of materials which are suitable as barrier layers are plastic films, nonwoven materials and different types of laminates. Useful plastic films are, for example, those which consist of polyethylene, polypropylene, or polyester. Optionally, the liquid-impervious cover layer 3 may consist of a laminate of a liquid-impermeable plastic layer facing the absorbent body, and a nonwoven layer facing the underclothing of the user. Such a construction provides a leakage-proof barrier layer with a textile feel. As is the case with the liquid-pervious cover layer 2, it is not necessary that the liquid-impervious cover layer 3 is constituted by a separate layer. Accordingly, it is conceivable that the liquid-impervious cover layer 3 constitutes an integral part of an absorbent material, for instance an absorbent foam layer with a liquid-impervious surface.

The absorbent body 4 may advantageously be constituted primarily by cellulose fluff pulp. This may be provided in the form of reels, bales or sheets which are dry shredded and in a fluffed state are transformed into a pulp mat, with or without the addition of so-called super-absorbents, which are polymers with the ability to absorb several times their own weight of water or body exudate. Examples of other useful materials are different types of natural fibres, such as cotton fibres, peat, or the like. It is, of course, also possible to utilize absorbent synthetic fibres, or blends of natural fibers and synthetic fibres. The absorption material may, furthermore, include additional components, such as liquid-distributing members or binders such as, for example, thermoplastic fibres which have been heat-treated in order to retain short fibres and particles as a coherent unit. It is also possible to utilize different types of absorbent foam material in the absorbent body 4.

The two cover layers 2, 3 are mutually connected outside the absorbent body 4 and form a protruding edge 5 around the entire periphery of the sanitary napkin. The joining the cover layers may be performed in any suitable way, for instance, by means of gluing, sewing, or welding with heat or ultrasonically.

The sanitary napkin 1 is substantially hourglass-shaped and thereby exhibits a front portion 6, intended to be turned forwards on the user during use, a rear portion 7, intended to be turned backwards on the user during use, and an intermediate, narrower crotch portion 8, intended to be applied in the grown area of the user. Furthermore, the sanitary napkin 1 has two concavely curved side edges 9, 10, a convexly curved front edge 11, and also a similarly convexly curved rear edge 12, The partition of the sanitary napkin into a front portion 6, a rear portion 7, and a crotch portion 8, should not be understood as if sharp limits exist between the different portions 6–8, but is primarily intended to facilitate the description of the sanitary napkin, starting from the differences which are present between the different portions 6–8 depending on how they are intended to be placed in relation to the body of a user. Thus, the transition between the different portions 6–8 does not take place at predetermined transverse lines, but rather within transition regions situated at a distance of approximately one third of the length of the sanitary napkin from the front edge 11 and the rear edge 12 of the sanitary napkin, respectively. Accordingly, the crotch portion 8 constitutes the part of the sanitary napkin which during use is intended to receive and absorb the main part of the liquid which is secreted to the sanitary napkin during use.

A stiffening element 15, for instance made of a rigid plastic layer, or a rigid metal plate, is arranged between the liquid-impervious cover layer 3 of the sanitary napkin 1 and the absorbent body 4, and extends across the front portion 6 and the crotch portion 8 of the sanitary napkin.

The stiffening element 15 is shaped as a spoon, or scoop, with a cupped part 16 situated at the front portion 6 of the sanitary napkin and a rectangular flat part 17 situated at the crotch portion 8. The cupped part 16 of the stiffening element 15 has substantially the same shape in the plane as the front portion 6 of the sanitary napkin, but is slightly smaller. Thereby, the parts of the front portion 6 which project past the edge 19 of the stiffening element 15 form a soft, cushioning edge region 18, which partly serves as a leakage seal, and partly counteracts chafing. In a corresponding way, the flat part 17 of the shape element 15 does not extend all the way out to the side edge 9, 10 of the sanitary napkin in the crotch portion 8, but a narrow, soft and resilient edge region 18, consisting of parts of the two cover layers 2, 3 and the absorbent body 4, extends between each respective side edge and the corresponding side edges 20, 21 on the stiffening element 15.

The cupped part 16 of the stiffening element 15 is angled in the longitudinal direction of the sanitary napkin in relation to the flat part 17, whereby also the front portion 6 of the sanitary napkin 1 is angled in relation to the crotch portion 8, as is best observed in FIG. 2. In order to obtain the desired angle of the sanitary napkin, the stiffening element 15 has been permanently curved, or bent along a transverse folding line 22, which is slightly curved in a direction towards the front edge of the sanitary napkin. The angle α, between the substantially flat crotch portion 8 of the sanitary napkin and the front portion 6 which is raised up from this, is thereby approximately 20°–50° and preferably approximately 30°. In FIG. 2, the angle α has been indicated on the outside of the sanitary napkin, i.e. the side of the sanitary napkin which in use is intended to be facing away from the user. The relevant angle is, however, in fact the angle on the inside of the sanitary napkin, since it is the inside which should conform to the anatomy of the user. In the shown example, it is of no importance if the angle is measured at the outside or the inside, since the value obtained will be the same, since both the front portion 6 and the crotch portion 8 have the same inclination on the inside as on the outside.

The curved folding line 22 contributes to providing the sanitary napkin with good shape stability and increases the bending stiffness of the stiffening element 15 at the folding line 22, since folding take place more easily along a straight line than along a curved line. Thereby, the angle between the cupped part 16 of the stiffening element 15 and its flat part 17 is maintained also when the sanitary napkin during use is subjected to force action. Furthermore, the folding line provides the front portion 6 of the sanitary napkin with a cupped appearance, as shown in FIG. 3, which is advantageous for fit and leakage security. At a width b of the front portion 6 which is between 80 and 100 mm, the curvature of the front portion 6 should not be larger than that a maximum deviation h, front a straight transverse line between the side edges 9, 10 of the sanitary napkin, does not exceed approx. 10 mm in the vicinity of the front edge 11.

Consequently, the front portion 6 of the sanitary napkin is angled in a direction towards the liquid-pervious cover layer 2, which implies that the front portion 6 is raised in the direction of the view, when the sanitary napkin is viewed with the liquid pervious cover layer 2 facing the viewer. Furthermore, the front portion 6 is advantageously curved along the longitudinal centre line 23 of the sanitary napkin, in such a way that the front portion 6 is bowl-shaped as seen from the liquid-pervious cover layer 2. However, the bowl-shape should not be more pronounced than that the longitudinal centre line deviates at the most 5 mm from a straight line extending along the cnetre line between the transverse folding line 22 and the front edge 11. A particular advantage with the cupped front portion is that it further increases the stability and the deformation resistance of the sanitary napkin. By means of the angle and the bowl-shape, the resistance to compression of the crotch portion 8 of the sanitary napkin is consequently increased.

It is advantageous if the angle of the front portion of the sanitary napkin, in an upward direction from the liquid-pervious cover layer 2, is permanent during use. This is achieved by making the stiffening element 15 of a material with a stiffness which in this context is to be considered as very high. For reasons of comfort, it is therefore necessary that the part of the stiffening element 15 which during use is intended to be applied in the groin area of the user is not so wide that is causes discomfort to the user. It is therefore essential that the width of the sanitary napkin does not exceed the critical value which can be tolerated by the users. For the sanitary napkin 1 shown in FIG. 1 this implies that the width of the flat portion 17 of the stiffening element 15 should not be larger than approx. 35 mm in an uncompressed condition. Even if the width of the crotch portion 6 of the sanitary napkin in tis entirety exceeds 35 mm this is, however, not critical, since the soft edge regions 18 around the stiffening element 15 permit certain compression and adaptation of the width of the sanitary napkin 1 according to the width of the groin of the user, whereby the width of the sanitary napkin after compressing does not exceed approx. 40 mm.

Furthermore, the material in the stiffening element 19 may be selected so that the stiffening element itself permits a certain compression transversely within the crotch portion 8. In order to achieve sufficiently high shape stability in the crotch portion 8, the stiffening element must, however, be sufficiently stiff to resist being compressed to more than 80% of its original width during normal conditions of use.

In the case that the stiffening element 19 is constituted by an extremely stiff material such as a, during normal conditions of use, totally inelastic plastic piece of material, or metal plate, it is especially important to adapt the width of the stiffening element 19 to the critical width of the groin of the user. When a completely inelastic stiffening element 19 is used, this should consequently not have a width which exceeds approx. 30 mm.

Figure 4:
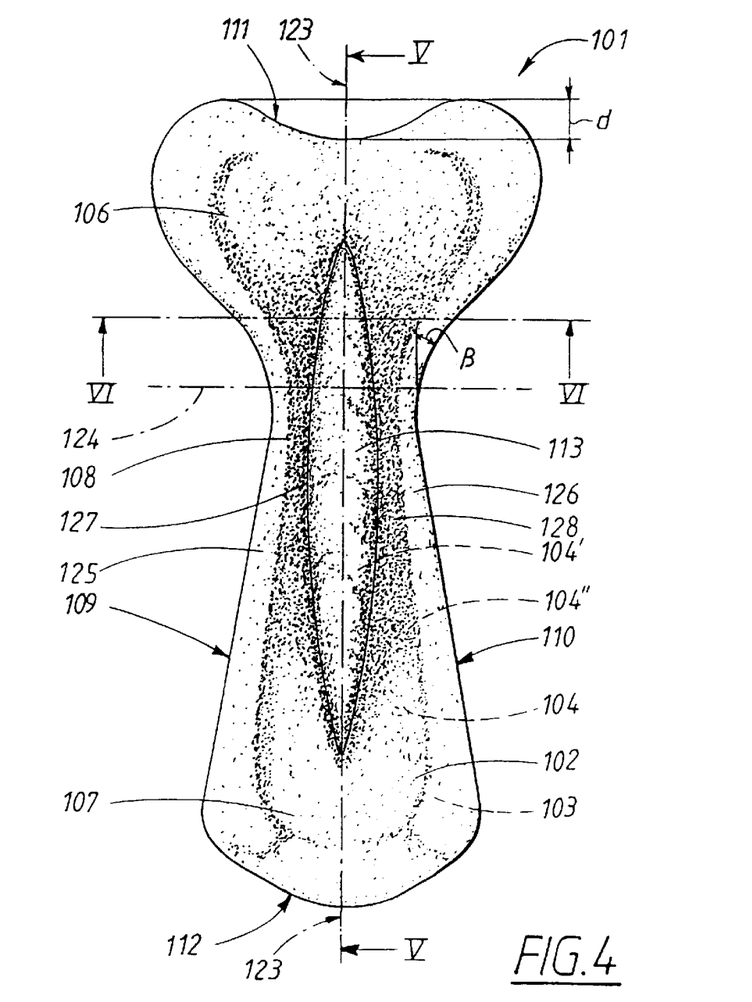
FIG. 4 shows a sanitary napkin according to an alternative embodiment of the invention.
Figure 5:
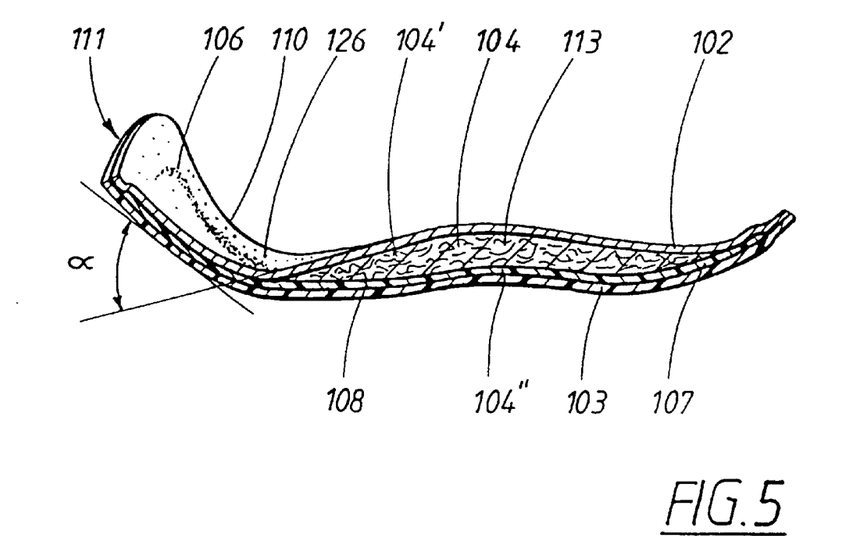
FIG. 5 shows a section along the line V—V through the sanitary napkin in FIG. 4 and FIG. 6, shows a section along the line VI—VI through the sanitary napkin in FIG. 4.
Figure 6:
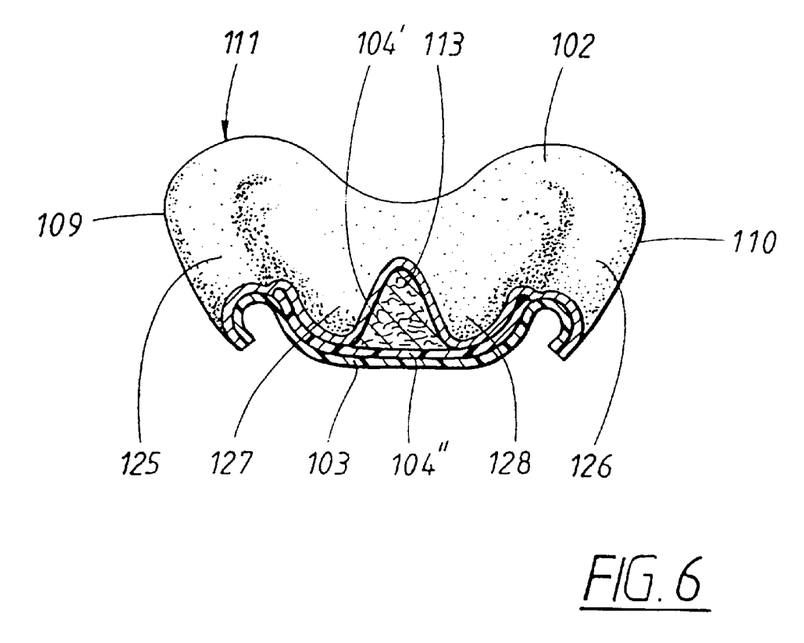

The sanitary napkin 101 shown in FIGS. 4, 5 and 6, comprises a liquid-pervious cover layer 102, and a liquid-impervious cover layer 103, which together enclose an absorbent body 104. The liquid-pervious cover layer 102 is, as in the sanitary napkin 1 shown in FIGS. 1, 2 and 3, constituted by a soft, flexible, skin-friendly material. The liquid-impervious cover layer 103, however, is constituted by a rigid material, preferably a comparatively thin, stiff plastic layer, which forms a hard, shape-retaining shell in which the absorbent body 104 is placed.

The sanitary napkin 101 is designed with a front portion 106 which is wider than a rear portion 107, and with a crotch portion 108 which is narrower then both the front portion and the rear portion. Due to the high stiffness of the liquid-impervious cover layer 103, it is essential that the sanitary napkin has a shape which, to a very high degree, is adapted to the anatomy of the user. Thereby, it is of particularly great importance that the width of the sanitary napkin, at least within the critical area of the crotch portion 108, does not exceed approx. 40 mm. As mentioned earlier, the critical area constitutes the part of the sanitary napkin which during use is intended to be arranged between the pace-limiting muscle groups which extend down on both sides in the crotch of the user. This area constitutes approx. 5 to 15 mm of the length of the crotch area 108.

Furthermore, the sanitary napkin 101 exhibits two longitudinal side edges 109, 110, a transverse concavely curved front edge 111 and a transverse convexly curved rear edge 112. The sanitary napkin is designed in such a way that, in the front part of the crotch portion 108 there is a cross-sectional line 124 extending, in the transverse direction of the sanitary napkin, which line intersects the side edges 109, 110 of the sanitary napkin. At the cross-sectional line 124, the side edges 109, 110 change inclination in relation to the longitudinal centre line 123, whereby the width of the sanitary napkin increases in a direction towards the front edge 111, whereby the front portion 106 exhibits a maximum width, which exceeds the width of the crotch portion 108 at the cross-sectional line 124. Thereby, the maximum width of the front portion 106 is preferably at least twice the width of the crotch portion 108 at the cross-sectional line 124. The inclination of the side edges 109, 110 at the front portion 106 is defined by an angle $\beta$ between each respective side edge 109, 110 and a longitudinal line parallel to the centre line 123, whereby $\beta$ is between 30° and 90° and whereby the width of the crotch portion 108 at the cross-sectional line 124 is between 15 and 45 mm and preferably between 20 and 40 mm. If, however, the sanitary napkin has a construction similar to the one which is shown in FIG. 1, the width of the sanitary napkin may be allowed to be up to 60 mm.

The absorbent body 104 comprises a first portion 104', which forms a longitudinal hump 113 on the side of the sanitary napkin which is use is intended to be facing a user. The first portion 104' consists of material with high absorption capacity, for instance absorbent fibres such as cellulose fluff pulp, rayon or the like, with or without super-absorbent material, absorbent foam or any of the above-described absorbent fibre materials. Furthermore, all conceivable types of mixtures and combinations of material layers may be used.

The absorbent body 104 of the sanitary napkin further comprises an absorption layer 104", arranged between the hump 113 and the liquid-impervious cover layer. The absorption layer 104" may consist of an absorbent non-woven material, tissue layer or any one of the above-mentioned absorbent materials and may, depending on the intended use of the sanitary napkin, be designed with larger or smaller absorption capacity.

In the sanitary napkin shown in FIGS. 4–6, the shape of the sanitary napkin is maintained by means of the entire liquid-impervious cover layer 103 constituting a shape-retaining shell for the absorbent body 104 of the sanitary napkin. As in the sanitary napkin in FIGS. 1–3, the front portion 106 of the sanitary napkin 101, shown in FIGS. 4–6, is angled in relation to the crotch portion 108 of the sanitary napkin. The angle α between the front portion 106 and the crotch portion 108 has in FIG. 5 been indicated as the angle between the inclination of the hump, along the longitudinal centre line 123 of the sanitary napkin, and the inclination of the front portion 106, since it is this inner angle which decides how well the sanitary napkin conforms to the shape of the body of the user in the relevant area. The upward bending of the front portion 106 in relation to the crotch portion 108 does not take place along a sharp folding line, but presents a continuous curvature in the longitudinal direction of the sanitary napkin. Thereby, the front portion 106 forms a softly rounded bowl which conforms very well to the anatomy of the user.

When estimating the angle α, the curvature of the front portion 106 is disregarded so that the inclination of the front portion is determined in relation to a straight line which extends along the longitudinal centre line 123, from an imaginary transverse border line between the front portion 106 and the crotch portion 108, to the front edge 111. Thereby, the exact value of the inclination of the front portion 106 in relation to the crotch portion is not critical, but the angle α should be between 20° and 50°. It is, however, advantageous if the angle α is maintained during use, both when the article is dry, and when it has been wetted by body fluid.

In FIG. 6, a cross-section through the sanitary napkin 101, shown in FIGS. 4 and 5, is shown. As is clearly evident from FIG. 6, the side edges 109, 110 of the sanitary napkin are curved in a direction downwardly-inwardly, as seen from the liquid-pervious cover layer 102. This implies that the sanitary napkin, along the side edges 109, 110, exhibits rounded ridges 125, 126 which during use of the sanitary napkin are intended to be in contact with the body of the user, in the groin folds of the user. The rounded ridges 125, 126 extend along the side edges 109, 110, along substantially the entire length of the sanitary napkin, but flatten out somewhat at the front edge 111 and the rear edge 112, respectively. Between the ridges 125, 126 and the hump 113, lowered furrows 127, 128 extend in which menstruation exudate maybe temporarily collected if it is not immediately absorbed into the absorbent body 104'.

According to a not shown embodiment, the furrows may be made deeper by providing the rigid liquid-impervious layer 103 with furrows. In such an embodiment, the longitudinal stiffness of the sanitary napkin is increased, at the same time as it becomes easier to compress the crotch portion. Accordingly, beams in the form of ridges and furrows increase the stiffness in the extension direction of the beams while, on the other hand, the stiffness in the perpendicular direction is reduced.

The raised ridges 125, 126, along the side edges 109, 110 of the sanitary napkin, fulfil several functions. On one hand, they constitute reinforcement beams which increase the bending resistance of the sanitary napkin when bending along substantially transverse bending lines, and on the other hand, the rounded surface which faces the user contributes to increase user comfort. Furthermore, the shaping of the stiff, liquid-impervious cover results in a certain degree of compressibility during use. Thereby, the raised ridges and the longitudinal ledges of the central hump 113 serve as notches, whereby compression of the crotch portion 108 may take place in a controlled manner. During use of the sanitary napkin, pressure forces from the thighs and groin of the user have the effect that the side edges 109, 110 of the sanitary napkin are pressed inwards in a direction towards the longitudinal centre line 123. What happens then is that the raised ridges 125, 126 are curved slightly inwards in a direction towards the hump 113. Consequently, the crotch portion 108 of the sanitary napkin generally maintains the shape it has been given in the production, even if the width of the crotch portion is slightly reduced by compression. A particular advantage is that no undesired further creasing, or other undesired deformation, of the crotch portion 108 takes place.

When liquid-impervious cover layers of, for example, polyethylene plastic or polypropylene plastic with a thickness of between approx. 0,5 mm and 1 mm are used, the formed crotch portion 108 exhibits high resiliency. Consequently, the crotch portion 108 substantially recovers its original shape and width so that the compression is discontinued. As in the sanitary napkin shown in FIGS. 1–3 it is, however, essential that the crotch portion always has a guaranteed minimum width during use, in order to avoid leakage. For this reason, the stiffness of the crotch portion must be sufficiently high that it is not compressed to more than approx. 80% of its original width during normal conditions of use.

In order to further increase the comfort for the user, the front portion 106 is provided with a recess at the front edge 111. The recess is formed by means of the front edge 111 being curved in a direction towards the crotch portion 108 of the sanitary napkin. Since the front edge 108 is concavely curved, it conforms to the outline of the mons veneris of the user in a better way, whereby the risk of chafing is almost non-existent.

EXAMPLE 1

In order to estimate the edge stiffness of an absorbent article, i.e. the resiliency of the article when it is subjected to compression in a transverse direction, the following test was performed:

The absorbent article was divided into two halves along the longitudinal centre line, whereafter one of the halves was clamped between two jaws mounted in an Instron tensile tester (1122, 4301, or 44664 with a 10 N cell) whereby the cut edge of the article was directed downwards between the jaws with the intact side edge freely protruding from the jaws. Thereafter, a metal rod having a cylinder mounted thereon was pressed perpendicularly against the edge at the region of the article which during use is arranged in the critical area in the crotch of the user. The force which was required in order to press down the edge was recorded by means of the tensile tester as a function of the down-pressed distance. The cylinder which was used to press against the edge was 40 mm long and had a diameter of 10 mm.

When the metal rod is pressed against the edge of the article an initial resistance arises. This is very distinct in the case of homogenous stiff materials such as plastic or hard paper. In the case of thicker, porous or fibrous materials, the edge splinters before it bends or cracks. Two force peaks are recorded for such materials.

As absorbent article such as a sanitary napkin, an incontinence guard, or a panty-liner may exhibit several stiff edges and consequently gives rise to several force peaks. The article may, for example, first have a welded edge joint, then a relatively soft and wide first absorbent core and thereafter a narrower, harder absorbent core. Absorbent articles with a shell, or a stiffening element of a resilient material such as a bent plastic layer, do not give rise to a distant force peak; instead, the impression force is almost proportional to the distance which the metal rod with the cylinder has been impressed.

In order for an absorbent article to have a sufficiently high resistance to transverse compression, it should not be possible during normal conditions of use to compress the crotch portion of the article more than that the width of the article is always at least approx. 15 mm and preferably is always at least approx. 20 mm. Furthermore, articles with a width which to begin with exceeds 40 mm should be easily compressed by means of the action of the forces which arise during use, so that the width during use does not exceed approx. 40 mm.

It proved to be difficult to exactly specify a force at which an absorbent article could be presumed to exhibit sufficient shape permanence. In order to estimate the magnitude of the force it must be taken into consideration that the recorded force varies depending on the above-mentioned factors, and also that it is difficult to accurately predict the force action which the article will be subjected to during use. The performed edge stiffness measurements, however, indicated that the force which is required to press the side edge of the article inwards a distance of 10 mm should be greater than approx. 20 N if an absorbent article according to the invention is to be regarded as having sufficient shape permanence.

For very stiff articles, for example with stiffening elements of metal, a measurement of the edge stiffness of course becomes meaningless. Accordingly, the method is primarily suited to determining whether an absorbent article has sufficient resistance to compression.

Materials such as paper, or heavily compressed fibre layers, which break when compressed so that they thereafter lose their ability to resist compression cannot be used of articles according to the invention.

EXAMPLE 2

The intrinsic stiffness of a number of flat materials was determined by means of the ASTM D 4032-82 Circular Bend Procedure, which method is described in detail in EP 0 336 578. The equipment consists of a rectangular plate which in the middle has a circular, funnel-shaped opening. The material is placed above the circular opening and is subjected to a force so that the material reaches down to the bottom of the plate. The force is measured and provides a value for the intrinsic stiffness of the material.

The materials which were found to have an intrinsic stiffness suitable for the purpose of the invention were materials for which a force of at least 100 N was recorded.

The invention should not be regarded as being limited to the herein described embodiments, but a number of further variants and modifications are conceivable within the scope of the claims. For instance, the invention comprises all types of absorbent articles which substantially are accommodated in the groin area of a user. Furthermore, all conceivable combinations of the descried embodiments are intended to be embraced by the invention.

What is claimed is:

1. Absorbent article which article has a generally elongated shape with a longitudinal direction and a transverse direction and exhibits two side edges, two end edges, two end portions and a crotch portion located between the end portions, which article furthermore exhibits a liquid-pervious cover layer, intended to be facing the user when worn, and a liquid-impervious cover layer, intended to be facing away from the user when worn, wherein the article at least within the crotch portion comprises a stiffening element of a material with a very high intrinsic stiffness so as to maintain substantial shape permanence of the article while worn by a user, whereby within at least a 5 mm extension of the crotch portion in the longitudinal direction, the article has an extension in the transverse direction which is between 15 mm and 40 mm while the article is worn by a user.

2. Absorbent article according to claim 1, wherein the stiffening element may only be compressed to approx. 80% of its original width during compression of the crotch portion in the transverse direction of the article with forces which occur while the article is worn by a user.

3. Absorbent article according to claim 1, wherein the stiffening element is profiled in the transverse direction of the article and exhibits at least one ridge, or furrow extending in the longitudinal direction.

4. Absorbent article according to claim 3, wherein a longitudinal ridge with a rounded surface is arranged along each side edge of the article at least line the crotch portion.

5. Absorbent article according to claim 1, wherein the stiffening element in the crotch portion on both sides of the stiffening element along the side edges of the article is surrounded by soft, easily deformable edge portions.

6. Absorbent article according to claim 1, wherein a force of at least 20 N is required in order to press one of the side edges of the article inwards a distance of 10 mm during compression perpendicularly to said one of the side edges.

7. Absorbent article according to claim 1, wherein the end portions are constituted by a front portion and a rear portion, wherein the article at least within the front portion and the crotch portion exhibits high bending resistance against bending along transversely extending bending lines, whereby the front portion and the crotch portion of the article exhibit high shape permanence while the article is worn by a user, and also that the front portion of the article is inclined in relation to the crotch portion, in a direction towards the liquid-pervious surface, whereby the front portion forms an angle α towards the crotch portion.

8. Absorbent article according to claim 7, wherein the article at least within the front portion and the crotch portion exhibit high bending resistance against bending along longitudinally extending bending lines.

9. Absorbent article according to claim 1, wherein the crotch portion of the article exhibits a transversely extending cross-sectional line, wherein the side edges of the article change inclination in relation to the longitudinal centre line of the article in the vicinity of the points of intersection between the cross-sectional line and the side edge, and from which cross-sectional line the width of the article increases in a direction towards the front edge, whereby the front portion exhibits a maximum width, which exceeds the width of the crotch portion at the cross-sectional line, wherein the tapered inclination of the side edges at the front portion is defined by means of an angle β between each respective side edge and a longitudinal line parallel to the centre line, wherein β is between 10° and 90°.

10. Absorbent article according to claim 1, wherein the liquid-impervious cover layer of the article is constituted by a liquid-impervious, stiff plastic layer whereby the liquid-impervious cover layer constitutes the stiffening member of the article.

11. Absorbent article according to claim 1, wherein the absorbent article is a sanitary napkin, an incontinence guard, or a panty-liner.

12. Absorbent article according to claim 1, wherein the article has an extension in the transverse direction which is between 20 mm and 35 mm while the article is worn by a user.

13. Absorbent article, which has a generally elongated shape with a longitudinal direction and a transverse direction and exhibits two side edges, two end edges, two end portions, and a crotch portion located between the end portions, which article furthermore exhibits a liquid-pervious cover layer, intended to be facing the user when worn, and a liquid-impervious cover layer, intended to be facing away from the user when worn, wherein the article at least within the crotch portion comprises a stiffening element of a material with an intrinsic stiffness of at least about 100 N.

14. Absorbent article, which has a generally elongated shape with a longitudinal direction and a transverse direction and exhibits two side edges, two end edges, two end portions, and a crotch portion located between the end portions, which article furthermore exhibits a liquid-pervious cover layer, intended to be facing the user when worn, and a liquid-pervious cover layer, intended to be facing away from the user when worn, wherein the article at least within the crotch portion comprises a stiffening element of a material with an intrinsic stiffness of at least about 100 N, whereby within at least a 5 mm extension of the crotch portion in the longitudinal direction, the article has an extension in the transverse direction which is between 15 mm and 40 mm while the article is worn by a user.

15. Absorbent article, which article has a generally elongated shape with a longitudinal direction and a transverse direction and exhibits two side edges, two end edges, two end portions, and a crotch portion located between the end portions, which article furthermore exhibits a liquid-pervious conver layer, intended to be facing the user when worn, and a liquid-impervious cover layer, intended to be facing away from the user when worn, wherein the article at least within the crotch portion comprises a stiffening element of a material with a very high intrinsic stiffness so as to maintain sufficiently high shape stability of the article while worn by a user, whereby within at least a 5 mm extension of the crotch portion in the longitudinal direction, the article has an extension in the transverse direction which is between 15 mm and 40 mm while the article is worn by a user.

16. Absorbent article according to claim 15, wherein the stiffening element may only be compressed to approx. 80% of its original width during compression of the crotch portion in the transverse direction of the article with forces which occur while the article is worn by a user.

* * * * *